United States Patent

Herbst et al.

(10) Patent No.: US 10,773,077 B2
(45) Date of Patent: Sep. 15, 2020

(54) METHODS AND DEVICES FOR PRODUCING TRABECULAR FIBERS

(71) Applicant: Boston Scientific Scimed Inc., Maple Grove, MN (US)

(72) Inventors: Thomas J. Herbst, Coon Rapids, MN (US); Craig M. Stolen, New Brighton, MN (US); Candace A. Rhodes, Walpole, MA (US)

(73) Assignee: Boston Scientific Scimed Inc, Maple Grove, MN (US)

( * ) Notice: Subject to any disclaimer, the term of this patent is extended or adjusted under 35 U.S.C. 154(b) by 334 days.

(21) Appl. No.: 15/712,542

(22) Filed: Sep. 22, 2017

(65) Prior Publication Data

US 2018/0147409 A1 May 31, 2018

Related U.S. Application Data

(60) Provisional application No. 62/426,995, filed on Nov. 28, 2016.

(51) Int. Cl.
*A61N 1/32* (2006.01)
*A61N 1/05* (2006.01)
(Continued)

(52) U.S. Cl.
CPC .......... *A61N 1/0573* (2013.01); *A61L 27/50* (2013.01); *A61L 27/54* (2013.01); *A61N 1/056* (2013.01); *A61N 1/326* (2013.01); *C12N 5/0657* (2013.01); *A61L 2300/41* (2013.01); *A61L 2300/42* (2013.01); *A61L 2430/20* (2013.01);
(Continued)

(58) Field of Classification Search
CPC .... A61N 1/0464; A61N 1/056; A61N 1/0565; A61N 1/0568; A61N 1/057; A61N 1/0573; A61N 1/0575; A61N 2001/0578; A61N 2001/205; A61N 2001/326; A61N 2001/362; A61N 2001/3627; A61N 2001/3629
See application file for complete search history.

(56) References Cited

U.S. PATENT DOCUMENTS

| 5,632,716 A | 5/1997 | Bui et al. |
| 2004/0186546 A1* | 9/2004 | Mandrusov ............ A61N 1/056 607/122 |

(Continued)

FOREIGN PATENT DOCUMENTS

| WO | WO0128455 A1 | 4/2001 |
| WO | 2005039691 A1 | 5/2005 |
| WO | 2017031238 A2 | 2/2017 |

OTHER PUBLICATIONS

Barile, Lucile, et al. "Human Cardiospheres as a Source of Multipotent Stem and Progenitor Cells." Stem Cells International, vol. 2013, Article ID 916837, 10 pages, Apr. 19, 2013.
Boston Scientific. "SpyGlass Direct Visualization System." Boston Scientific, 12 pages, Apr. 2013.
Cigna. "Cigna HealthCare Coverage Position: Partial Left Ventriculectomy Dynamic Cardiomyoplasty and Ventricular Reshaping in the Treatment of Heart Failure." Cigna, revised Mar. 15, 2006, 10 pages.

(Continued)

*Primary Examiner* — Eugene T Wu
(74) *Attorney, Agent, or Firm* — Faegre Drinker Biddle & Reath LLP

(57) ABSTRACT

A device for producing a trabecular fiber within a ventricle of a heart. The device includes a substrate and a first tissue anchor connected to the substrate. The substrate is formed of a non-rigid material.

7 Claims, 9 Drawing Sheets

(51) Int. Cl.
    *A61L 27/50*     (2006.01)
    *A61L 27/54*     (2006.01)
    *C12N 5/077*     (2010.01)
    *A61N 1/20*     (2006.01)

(52) U.S. Cl.
    CPC ......... *A61L 2430/30* (2013.01); *A61N 1/0568* (2013.01); *A61N 1/205* (2013.01)

(56) References Cited

U.S. PATENT DOCUMENTS

| | | | |
|---|---|---|---|
| 2006/0129216 A1* | 6/2006 | Hastings | A61B 5/0215 607/115 |
| 2007/0106201 A1* | 5/2007 | Soykan | C12N 5/0657 604/20 |
| 2011/0082538 A1 | 4/2011 | Dahlgren et al. | |
| 2011/0237967 A1* | 9/2011 | Moore | A61B 5/042 600/509 |
| 2012/0251508 A1 | 10/2012 | Basu et al. | |
| 2013/0231727 A1 | 9/2013 | Carlson et al. | |
| 2015/0088155 A1* | 3/2015 | Stahmann | A61N 1/3756 606/129 |
| 2015/0306381 A1* | 10/2015 | Schmidt | A61B 17/50 607/120 |
| 2017/0050018 A1* | 2/2017 | Herbst | A61N 1/056 |

OTHER PUBLICATIONS

Grandjean, P. A., et al. "Long-Term Outcome of Dynamic Cardiomyoplasty in France." Basic Applied Myology, 19 (1):17-24, 2009.

International Search Report and Written Opinion issued in PCT/US2016/047413, dated Nov. 28, 2016, 7 pages.

International Search Report and Written Opinion issued in PCT/US2017/052909, dated Dec. 13, 2017, 14 pages.

Makkar, Raj R., et al. "Intracoronary Cardiosphere-Derived Cells for Heart Regeneration After Myocardial Infarction (CADUCEUS): A Prospective, Randomised Phase 1 Trial." Lancet, 379:895-904, Mar. 10, 2012.

Messina, Elisa, et al. "Isolation and Expansion of Adult Cardiac Stem Cells From Human and Murine Heart." Cellular Biology, Circ. Res., 95:911-921 and Supplemental Material, 22 pages, 2004.

Smith, Rachel Ruckdeschel, et al. "Regenerative Potential of Cardiosphere-Derived Cells Expanded From Percutaneous Endomyocardial Biopsy Specimans." Circulation, 115:896-908, 2007.

Ye, Lei, et al. "Patching the Heart: Cardiac Repair From Within and Outside." Circulation Research, 113:922-932, 2013.

Zoler, Mitchel. "The Surgery Was a Success, but the Device Died." EGMN: Notes from the Road [online], Mar. 24, 2010, retrieved from https://egmnblog.wordpress.com/2010/03/24/the-surgery-was-a-success-but-the-device-died/, 3 pages.

* cited by examiner

METHODS AND DEVICES FOR PRODUCING TRABECULAR FIBERS

CROSS-REFERENCE TO RELATED APPLICATION

This application claims priority to Provisional Application No. 62/426,995, filed Nov. 28, 2016, which is herein incorporated by reference in its entirety.

TECHNICAL FIELD

The present invention relates to medical devices and methods for producing de novo trabecular fibers. More specifically, the invention relates to devices and methods producing trabecular fibers to repair a heart in a minimally-invasive manner.

BACKGROUND

Millions of people suffer from a weakened or damaged heart resulting in impaired cardiac output. For example, some people may suffer from dilated cardiomyopathy resulting in a thinning, weakened ventricular heart wall. The weakened heart wall may not be able to pump blood efficiently. Other people may have gaps from a misalignment in the heart valve leaflets resulting in regurgitation. Regurgitation of the heart valve may also result in less efficient pumping of blood. Still other people may suffer damage to the ventricular heart wall from ischemia or a myocardial infarction. The damaged heart wall usually heals by fibrosis, with nonfunctional connective scar tissue replacing the lost cardiac cells (conductile or contractile). The loss of heart cells and replacement by scar tissue is a suboptimal repair. This typically results in a condition where the heart may not be able to pump blood efficiently. Any of these diseases may result in impaired cardiac output.

Current methods of treating heart diseases, such as those mentioned above, and others, can be highly invasive. Invasive treatments may include, for example, implanting an artificial heart pump, or coronary artery bypass grafting (CABG) requiring open-chest surgery. The treatments often require pharmacologic intervention with cardiac drugs. Ultimately, such treatments may lead to less than optimal clinical outcomes, achieving only minimal improvement in cardiac output for the patient. What is needed is a way to repair a heart in a minimally-invasive manner, leveraging and amplifying intrinsic repair mechanisms.

SUMMARY

Example 1 is a device for producing a trabecular fiber within a ventricle of a heart. The device includes a substrate and a first tissue anchor connected to the substrate. The substrate is formed of a non-rigid material.

Example 2 is the device of Example 1, wherein the device is configured to be contained entirely within the ventricle.

Example 3 is the device of either of Examples 1 or 2, wherein the substrate includes a ribbon of electro-spun fibers.

Example 4 is the device of, any of Examples 1-3, wherein the substrate is formed of at least one of a polyurethane polymer, a polyester polymer, a silicone polymer, a styrene-isobutylene-styrene block copolymer, an expanded polytetrafluoroethylene polymer, collagen, hyaluronan, cellulose, fibrin, fibrinogen, and fibronectin.

Example 5 is the device of any of Examples 1-4, wherein the substrate includes at least one electrode disposed on the substrate.

Example 6 is the device of either of Examples 1 or 2, wherein the substrate includes at least one helically wound conductive coil forming at least one electrode.

Example 7 is the device of either of Examples 5 or 6, wherein the device is configured to be connected to a pulse generator and a power supply external to the heart by an electrical lead, the electrical lead connecting the pulse generator and the power supply to the at least one electrode to generate a plurality of voltage pulses at the at least one electrode.

Example 8 is the device of either of Examples 5 or 6, wherein the device further includes a pulse generator and a power supply, the pulse generator and the power supply electrically connected to the at least one electrode to generate a plurality of voltage pulses at the least one electrode.

Example 9 is the device of any of Examples 1-8, further including a second tissue anchor connected to the substrate opposite the first tissue anchor.

Example 10 is the device of any of Examples 1-9, further including at least one drug eluting collar disposed around the substrate, the drug eluting collar including an anti-inflammatory or immunosuppressive biologic or pharmaceutical agent.

Example 11 is a method for producing at least one trabecular fiber within a ventricle of a heart to repair the heart. The method includes inserting a device entirely within a heart, the device including a flexible substrate and at least one tissue anchor connected to the substrate; anchoring the inserted device within the heart by securing the at least one tissue anchor to an endocardium, the substrate not in contact with the endocardium; and maintaining the anchored device within the heart for a time at least sufficient to form at least one trabecular fiber extending between the substrate and the endocardium, the at least one trabecular fiber including cardiomyocyte cells, wherein the substrate and at least one trabecular fiber are disposed to repair the heart.

Example 12 is the method of Example 11, wherein maintaining the device within the heart includes producing an electrical potential between an electrode on the substrate and the endocardium.

Example 13 is the method of either of Examples 11 or 12, wherein a plurality of trabecular fibers are formed, a first portion of the plurality of trabecular fibers disposed to repair the heart and a second portion of the plurality of trabecular fibers not disposed to repair the heart, the method further including cutting away the second portion of the plurality of trabecular fibers from the endocardium, cutting away the second portion of the trabecular fibers from the substrate, and removing the second portion of the trabecular fibers from the heart.

Example 14 is the method of any of Examples 11-13, wherein the device is inserted into a right ventricle of the heart.

Example 15 is the method of any of Examples 11-14, wherein maintaining the device within the heart includes eluting an anti-inflammatory or immunosuppressive biologic or pharmaceutical agent from a drug eluting collar disposed around the substrate.

Example 16 is a device for producing a trabecular fiber within a ventricle of a heart. The device includes a substrate and a first tissue anchor connected to the substrate. The substrate is formed of a non-rigid material. The device is configured to be contained entirely within the ventricle.

Example 17 is the device of Example 16, wherein the substrate includes a ribbon of electro-spun fibers.

Example 18 is the device of Example 16, wherein the substrate is formed of at least one of a polyurethane polymer, a polyester polymer, a silicone polymer, a styrene-isobutylene-styrene block copolymer, an expanded polytetrafluoroethylene polymer, collagen, hyaluronan, cellulose, fibrin, fibrinogen, and fibronectin.

Example 19 is the device of Example 16, wherein the substrate includes at least one electrode.

Example 20 is the device of Example 19, wherein the device is configured to be connected to a pulse generator and a power supply external to the heart by an electrical lead, the electrical lead connecting the pulse generator and the power supply to the at least one electrode to generate a plurality of voltage pulses at the at least one electrode.

Example 21 is the device of Example 19, wherein the device further includes a pulse generator and a power supply, the pulse generator and the power supply electrically connected to the at least one electrode to generate a plurality of voltage pulses at the least one electrode.

Example 22 is the device of Example 16, further including a second tissue anchor connected to the substrate opposite the first tissue anchor.

Example 23 is the device of Example 16, further including at least one drug eluting collar disposed around the substrate, the collar including a steroid.

Example 24 is a device for producing a trabecular fiber within a ventricle of a heart. The device includes a substrate and a first tissue anchor connected to the substrate. The substrate is formed of at least one helically wound conductive coil. The device is configured to be contained entirely within the ventricle.

Example 25 is the device of Example 24, wherein the at least one helically wound conductive coil forms an electrode.

Example 26 is the device of Example 25, wherein the device is configured to be connected to a pulse generator and a power supply external to the heart by an electrical lead, the electrical lead connecting the pulse generator and the power supply to the at least one electrode to generate a plurality of voltage pulses at the at least one electrode.

Example 27 is the device of Example 25, wherein the device further includes a pulse generator and a power supply, the pulse generator and the power supply electrically connected to the at least one electrode to generate a plurality of voltage pulses at the least one electrode.

Example 28 is a method for producing at least one trabecular fiber within a ventricle of a heart to repair the heart, the method including inserting a device entirely within a ventricle of a heart, the device including a flexible substrate and at least one tissue anchor connected to the substrate; anchoring the inserted device within the heart by securing the at least one tissue anchor to an endocardium, the substrate not in contact with the endocardium; and maintaining the anchored device within the heart for a time at least sufficient to form at least one trabecular fiber extending between the substrate and the endocardium, the at least one trabecular fiber including cardiomyocyte cells, wherein the substrate and the at least one trabecular fiber are disposed to repair the heart.

Example 29 is the method of Example 28, wherein maintaining the device within the heart includes producing an electrical potential between an electrode on the substrate and the endocardium.

Example 30 is the method of Example 29, wherein the electrical potential is produced as a series of electrical pulses.

Example 31 is the method of Example 28, wherein the device remains within the heart after the device has been maintained in the heart for a time at least sufficient to form a plurality of trabecular fibers extending between the substrate and the endocardium.

Example 32 is the method of Example 28, wherein a plurality of trabecular fibers are formed, a first portion of the plurality of trabecular fibers disposed to repair the heart and a second portion of the plurality of trabecular fibers not disposed to repair the heart, the method further including cutting away the second portion of the plurality of trabecular fibers from the endocardium, cutting away the second portion of the trabecular fibers from the substrate, and removing the second portion of the trabecular fibers from the heart.

Example 33 is the method of Example 27, wherein anchoring the device within the heart includes securing a first tissue anchor and a second tissue anchor to the endocardium.

Example 34 is the method of Example 27, wherein the device is inserted into a right ventricle of the heart.

Example 35 is the method of Example 27, wherein maintaining the device within the heart includes eluting a steroid from a drug eluting collar disposed around the substrate While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
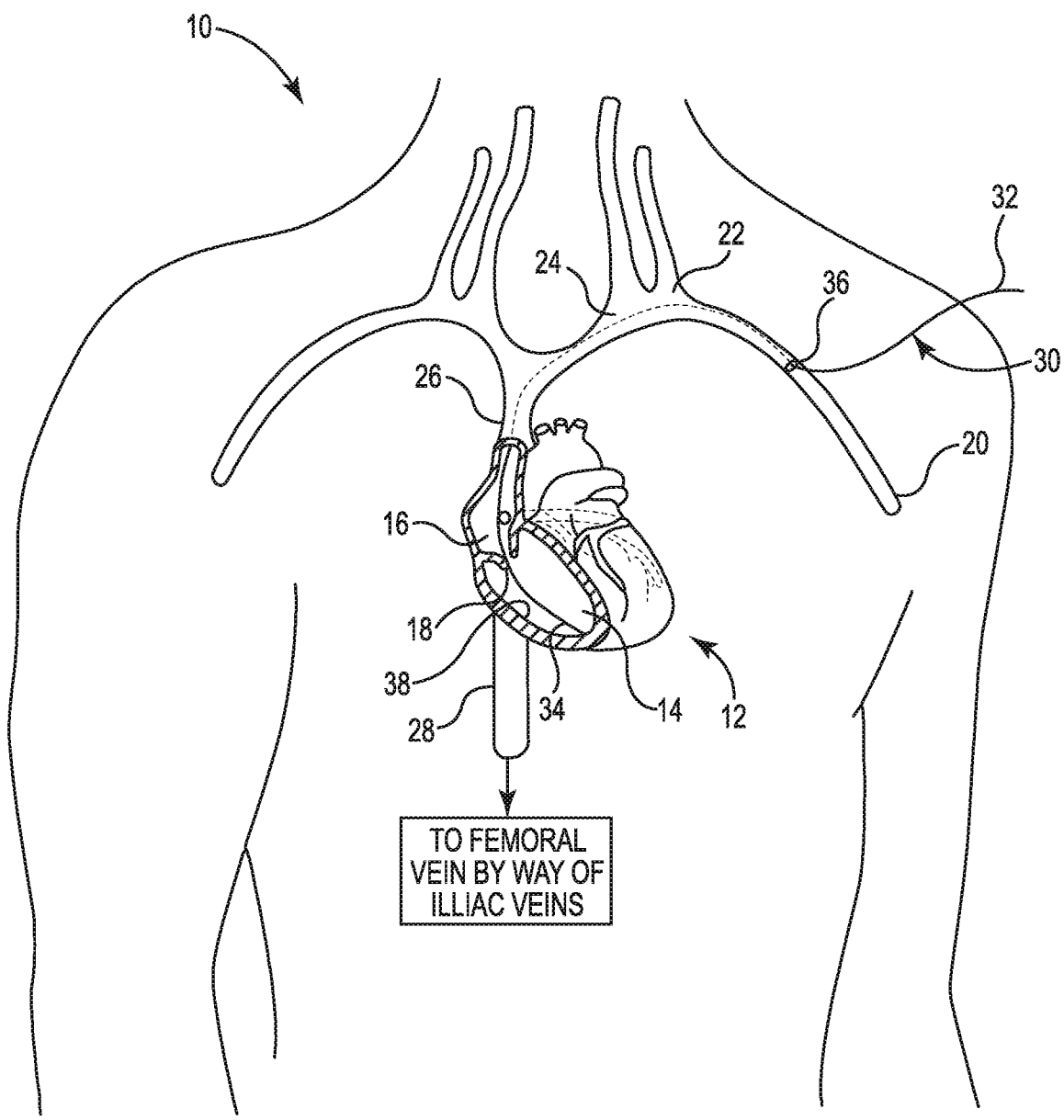
FIG. 1 is a schematic view illustrating the implantation of a device for stimulating the growth of at least one de novo trabecular fiber, in accordance with embodiments of the present disclosure.

FIG. 1 is a schematic view illustrating the implantation of a device for producing at least one trabecular fiber within a heart to help repair the heart, in accordance with embodiments of the present invention. The at least one trabecular fiber includes new contractile or conductile heart muscle tissue, or cardiomyocyte cells. The trabecular fiber produced as described herein includes new cardiomyocyte cells grown de novo within the heart chamber, and not pre-existing heart tissue simply rearranged. Together, the device and attached at least one trabecular fiber may repair the heart by connecting to various structures encircling a ventricle, such as a ventricle wall, a septum, and a valve, to strengthen and/or reshape the heart. In some embodiments, the de novo trabecular fiber may serve as a moderator band in those without this anatomical feature to limit sudden dilation due to fluctuating venous return, aid in synchronizing right ventricle free wall depolarization to treat conduction delays, and/or provide collateral blood flow.

FIG. 1 is a schematic view illustrating the implantation of a device for producing at least one trabecular fiber within a heart. FIG. 1 illustrates a patient 10 including a heart 12. The heart 12 includes a right ventricle 14, a right atrium 16, and a tricuspid valve 18 separating the right atrium 16 from the right ventricle 14. Also shown in FIG. 1 are veins directing blood to the heart 12 including a left auxiliary vein 20, which flows into a left subclavian vein 22, which flows into a left brachiocephalic vein 24. The left brachiocephalic vein 24 flows into a superior vena cava 26, which supplies blood to the right atrium 16 from the upper part of the body. An inferior vena cava 28 receives blood from a femoral vein (not shown) by way of an external iliac vein (not shown) and a common iliac vein (not shown). The inferior vena cava 28 also supplies blood to the right atrium 16.

FIG. 1 shows a catheter 30 having a proximal end 32 and a distal end 34. In some embodiments, the catheter 30 may enter the left auxiliary vein 20 percutaneously through a vascular entry site 36. The distal end 34 may be maneuvered through a left auxiliary vein 20, the left subclavian vein 22, the left brachiocephalic vein 24, the superior vena cava 26, and into the heart 12 at the right atrium 16. In other embodiments, the catheter 30 may percutaneously enter the femoral artery. The distal end 34 may be maneuvered through the external iliac vein, the common iliac vein, the inferior vena cava 28, and into the heart 12 at the right atrium 16. In either embodiment, the distal end 34 may be maneuvered from the right atrium 16, through the tricuspid valve 18, and into the right ventricle 14. The catheter 30 may include at least one lumen (not shown) extending from the proximal end 32 to the distal end 34 through which instruments (not shown) may be used to implant a device into an endocardium 38 lining the walls of the right ventricle 14, such as a device 40 for producing at least one trabecular fiber within the heart 12 as described below in reference to FIG. 2. As described above, implantation of device 40 is done in a minimally-invasive manner.

Figure 2:
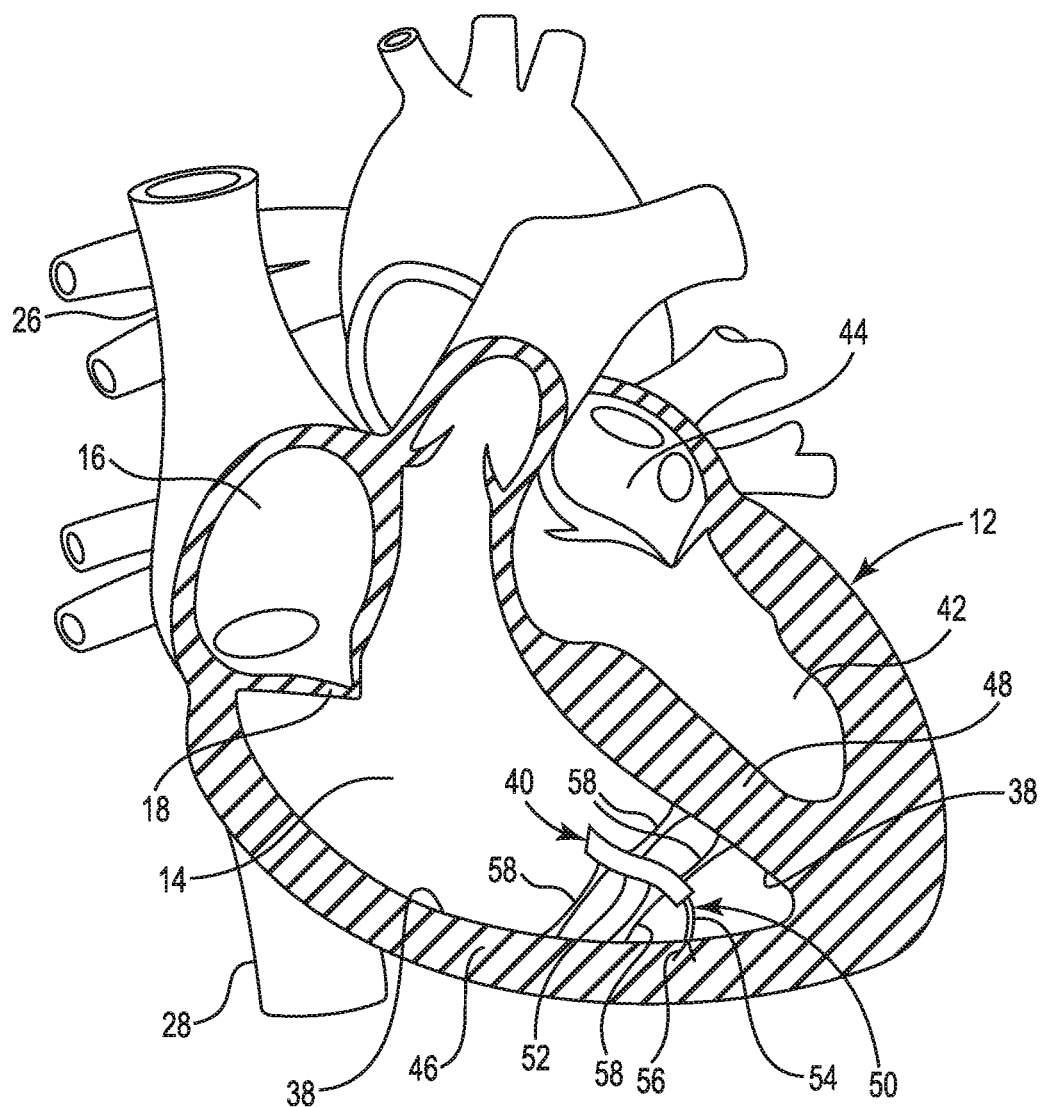
FIG. 2 is a schematic view of a portion of the patient's heart further illustrating implanted device of FIG. 1, in accordance with embodiments of the present disclosure.

FIG. 2 is an enlarged schematic view of the heart 12 of FIG. 1. As shown in FIG. 2, the heart 12 further includes left ventricle 42, left atrium 44, ventricular wall 46, and septum 48 between the right ventricle 14 and the left ventricle 42. FIG. 2 illustrates the device 40, according to some embodiments, implanted into the endocardium 38 of the ventricular wall 46. As shown in FIG. 2, the device 40 includes a tissue anchor 50 and a substrate 52. The tissue anchor 50 can include a linking section 54 and a fixation device 56. The linking section 54 connects the fixation device 56 to the substrate 52, connecting the tissue anchor 50 to the substrate 52.

In some embodiments, the substrate 52 is a flexible, non-rigid ribbon or sheet made at least in part from a biocompatible polymer, for example, a polyurethane polymer, a polyester polymer, silicone polymer, a styrene-isobutylene-styrene block copolymer, or an expanded polytetrafluoroethylene polymer. Alternatively or additionally, the substrate 52 may be made at least in part of an organic substance, for example, collagen, hyaluronan, cellulose, fibrin, fibrinogen, or fibronectin. In some embodiments, the substrate 52 may be a solid or may be an electro-spun mesh of a biocompatible polymer and/or an organic substance. In some embodiments, the linking section 54 of the tissue anchor 50 can be made of any of the above mentioned biocompatible polymers or organic substances. The fixation device 56 may be a passive fixation device, such as tines as illustrated in FIG. 2, or an active fixation device, such as a hook or helical configuration to bore into a heart wall, such as the ventricular wall 46 or the septum 48.

As shown in FIG. 2, the fixation device 56 of the tissue anchor 50 is secured into the endocardium 38 and the ventricular wall 46 to anchor the device 40 within the right ventricle 14 of the heart 12 such that the substrate 52 is spaced apart from endocardium 38. As the device 40 is maintained in the heart 12, at least one de novo trabecular fiber 58 forms between the endocardium 38 and the substrate 52. In the embodiment shown in FIG. 2, a plurality of trabecular fibers 58 are formed. In the embodiment shown in FIG. 2, the trabecular fibers 58 extending between the substrate 52 and ventricular wall 46, and the trabecular fibers 58 extending between the substrate 52 the septum 48 serve to connect the ventricular wall 46 to the septum with the new contractile or conductile heart muscle tissue. So disposed, the substrate 52 and the trabecular fibers 58 with their contractile or conductile heart muscle tissue can serve to strengthen the ventricular wall to repair damage due to thinning of the ventricular wall 46 or to an infarction in the ventricular wall 46.

Figure 3:
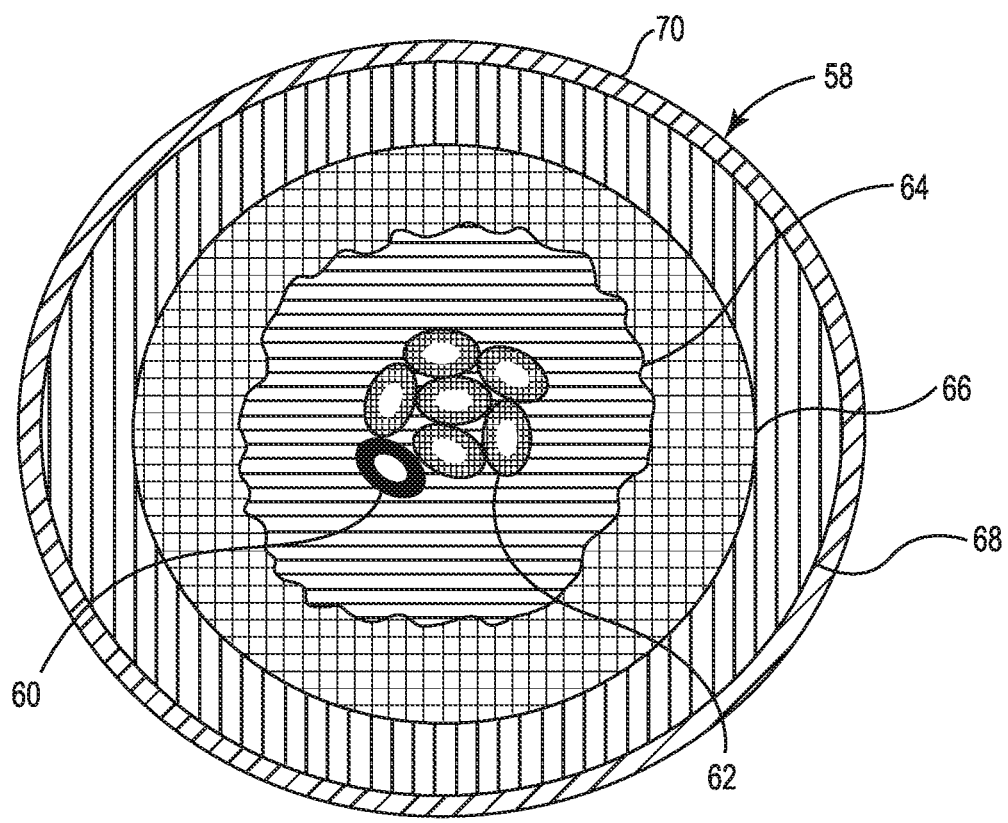
FIG. 3 is a schematic cross-sectional view of a de novo trabecular fiber containing cardiomyocyte cells.

FIG. 3 is a schematic cross-sectional view of the trabecular fiber 58. In the particular illustrated embodiment, the trabecular fiber 58 includes a blood vessel 60, a plurality of cardiomyocyte cells 62, an extracellular matrix layer 64, an elastin layer 66, an outer collagen layer 68, and an endothelial cell layer 70. The cardiomyocyte cells 62 can be disposed at a core of the trabecular fiber 58 and can be generally oriented with their long-axis (not shown) parallel to the length of the trabecular fiber 58 (FIG. 2). The cardiomyocyte cells 62 can be embedded in an extracellular matrix formed by the extracellular matrix layer 64, and may be nourished by the blood vessel 60 coursing in parallel to the cardiomyocyte cells 62 and/or by blood within the right ventricle 14 (FIG. 2). The outer collagen layer 68 can be an external layer of the trabecular fiber 58. The elastin layer 66 can be disposed between the extracellular matrix layer 64 and the outer collagen layer 68. Although the trabecular fiber 58 layers are illustrated with distinct boundaries, it is understood that there can be mixing of the layers at their respective interfaces. The overall organizational histologic architecture of the trabecular fiber 58 is that of a tube (the cardiomyocyte cells 62), within a tube (the elastin layer 66), within a tube (the outer collagen layer 68). The presence of the cardiomyocyte cells 62 at the core of the trabecular fiber 58 distinguishes the trabecular fiber 58 from structures of somewhat similar appearance, such as chordae tendineae of the tricuspid valve 18 (FIG. 1). Without wishing to be bound by any theory, it is believed that the presence of the device 40 in the dynamic environment of the right ventricle 14 produces mechanical stresses on the endocardium 38 of the heart 12. It is believed that these stresses, possibly caused by the movement of the substrate 52, stimulate the growth of the trabecular fiber 58 including the core of cardiomyocyte cells 62. It is also believed that this growth is further stimulated by the flexible, non-rigid structure of the substrate 52 which produces greater movement, according to some embodiments. It is further believed that the substrate 52 creates a stimulus for the development of a provisional matrix connected to the substrate 52, the provisional matrix composed of fibrinogen, red cells, platelets, white cells and, in some embodiments, stem or progenitor cells. It is believed that the white cells may be leukoscytes, such as macrophages and/or T cells. It is believed that the stem or progenitor cells may be bone marrow derived or resident cells within the endocardium 38 of the right ventricle 14. It is believed that the provisional matrix facilitates the growth and propagation of cells to create an immature de novo trabecular fiber which matures into the contractile/conductile functioning trabecular fiber 58.

Figure 4:
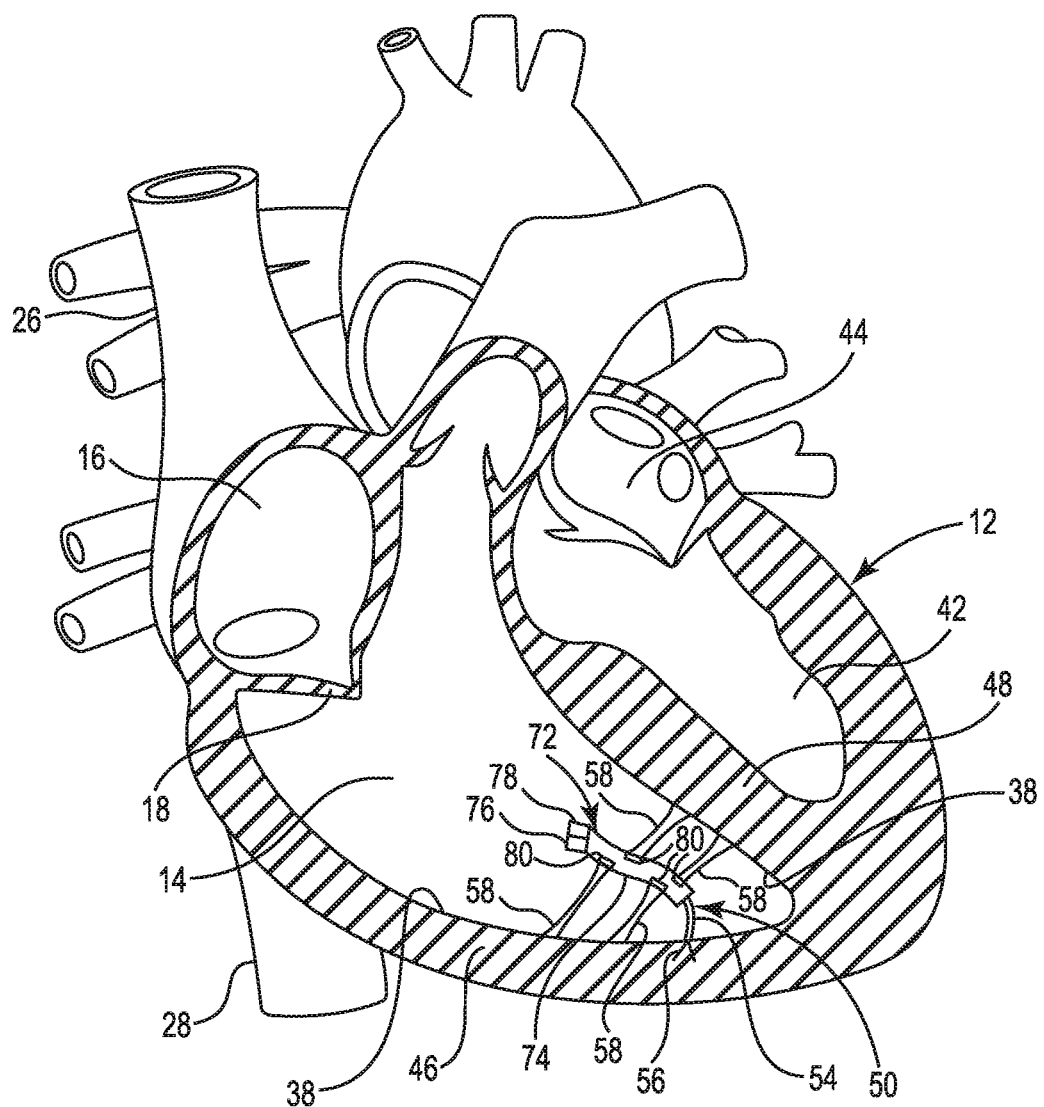
FIG. 4 is an enlarged schematic view of the heart 12 of FIG. 1 illustrating another device for stimulating the growth of at least one trabecular fiber, in accordance with embodiments of the present disclosure.

FIG. 4 is an enlarged schematic view of the heart 12 of FIG. 1 illustrating another embodiment. FIG. 4 illustrates a device 72, according to some embodiments, implanted into the endocardium 38 of the ventricular wall 46. As shown in FIG. 4, the device 72 includes a tissue anchor 50, a substrate 74, a power supply 76, and pulse generator 78. The substrate 74 can be substantially similar to substrate 40 described above, except that it includes at least one electrode 80 (four shown in FIG. 4) disposed on the substrate 74. The power supply 76 can include a battery. The pulse generator 78 is electrically connected to the power supply 76 and to the at least one electrode 80 so that together, the power supply 76 and the pulse generator 78 generate a plurality of voltage pulses at the at least one electrode 80. The pulse generator 78 can control characteristics of the plurality of voltage pulses, for example, the frequency of the pulses, the length of the pulses, and the amplitude of the pulses. Such pulse generators are well known in the art. The at least one electrode 80 can be made of any conductive, biocompatible material, for example, titanium, platinum, stainless steel, nitinol, iridium, or iridium oxide. In some embodiments, the at least one electrode 80 is disposed on a surface of the substrate 74.

As with device 40 described above, the tissue anchor 50 can include a linking section 54 and a fixation device 56. The linking section 54 connects the fixation device 56 to the substrate 74, connecting the tissue anchor 50 to the substrate 74. In the embodiment shown in FIG. 4, the power supply 76 and the pulse generator 78 are disposed at an end of the substrate 74. However, in other embodiments, the power supply 76 and the pulse generator 78 can be disposed anywhere along the substrate 74 or the anchor 50.

As shown in FIG. 4, the fixation device 56 of the tissue anchor 50 is secured into the endocardium 38 to anchor the device 72 within the heart 12 such that the substrate 74 is spaced apart from endocardium 38. Voltage pulses can be generated from the at least one electrode 80 to produce an electrical potential between the substrate 74 and the endocardium 38. As the device 72 is maintained in the heart 12, at least one trabecular fiber 58 forms between the endocardium 38 and the substrate 74. In the embodiment shown in FIG. 4, a plurality of trabecular fibers 58 are formed. In the embodiment shown in FIG. 4, the trabecular fibers 58 extending between the substrate 74 and ventricular wall 46, and the trabecular fibers 58 extending between the substrate 74 the septum 48 serve to connect the ventricular wall 46 to the septum with the new contractile/conductile heart muscle tissue. So disposed, the substrate 74 and the trabecular fibers 58 with their contractile heart muscle tissue can serve to repair damage due to thinning of the ventricular wall 46 or to an infarction in the ventricular wall 46, thus improving cardiac output. Not wishing to be bound by any theory, it is believed that the voltage pulses at the at least one electrode 80 may further stimulate the growth of the trabecular fibers 58. In the embodiment shown in FIG. 4, the trabecular fibers 58 are shown attached to the substrate 74 at the electrodes 80. However, in other embodiments, the trabecular fibers 58 may attach elsewhere on the substrate 74.

Figure 5:
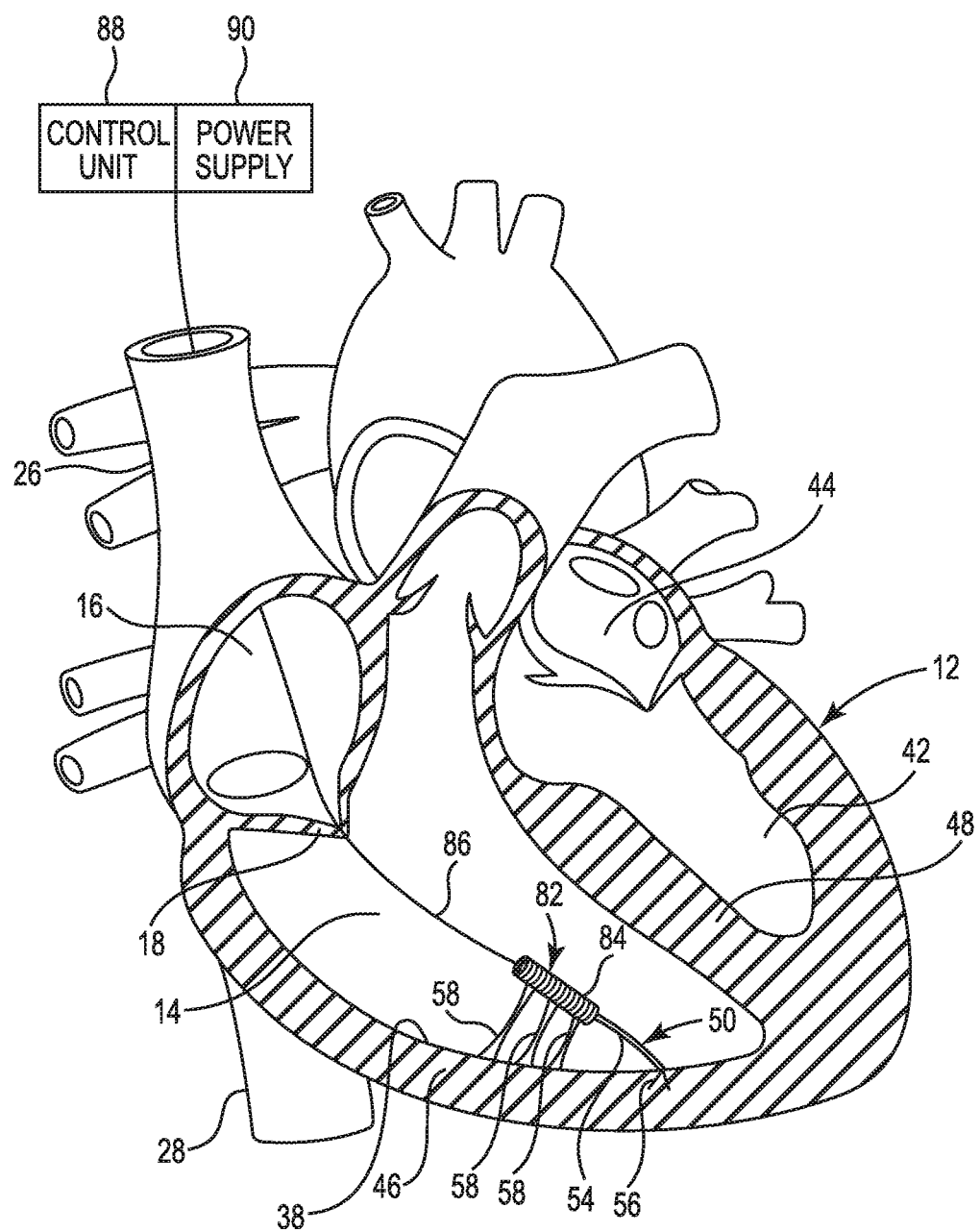
FIG. 5 is an enlarged schematic view of the heart 12 of FIG. 1 illustrating another device for stimulating the growth of at least one trabecular fiber, in accordance with embodiments of the present disclosure.

FIG. 5 is an enlarged schematic view of the heart 12 of FIG. 1 illustrating another embodiment. FIG. 5 illustrates a device 82, according to some embodiments, implanted into the endocardium 38 of the ventricular wall 46. As shown in FIG. 5, the device 82 includes a tissue anchor 50, and a substrate 84. As with devices 40 and 72 described above, the tissue anchor 50 can include a linking section 54 and a fixation device 56. The linking section 54 connects the fixation device 56 to an end of the substrate 84, connecting the tissue anchor 50 to the substrate 84.

In some embodiments, the substrate 84 is a flexible, non-rigid, helically wound conductive coil made at least in part from a biocompatible conductor, for example, titanium, platinum, stainless steel, nitinol, iridium, or iridium oxide. In some embodiments, the coil turns can be closely spaced such that adjacent turns are in physical contact for improved MRI compatibility. In other embodiments the coil turns can be more widely spaced to provide larger gaps between adjacent turns to enhance adhesion of the trabecular fibers to the substrate 84.

As shown in the embodiment of FIG. 5, an end of the substrate 84 can be electrically and physically connected to an electrical lead 86 extending from the device 82, through the tricuspid valve 18, the right atrium 16 and out of the heart 12 to a pulse generator 88 and a power supply 90 external to the heart 12. In some embodiments, the pulse generator 88 and the power supply 90 can be disposed in a subcutaneous pocket (not shown) adjacent to the vascular entry site 36 (FIG. 1). As with devices 40 and 72 described above, the tissue anchor 50 can include a linking section 54 and a fixation device 56. The linking section 54 connects the fixation device 56 to the substrate 44, connecting the tissue anchor 50 to the substrate 44.

The power supply 90 can include a battery. The pulse generator 88 is electrically connected to the power supply 90 and to the substrate 84 so that together, the power supply 90 and the pulse generator 88 generate a plurality of voltage pulses at the substrate 84, which functions as an electrode. The pulse generator 88 can control characteristics of the plurality of voltage pulses, for example, the frequency of the pulses, the length of the pulses, and the amplitude of the pulses. Such pulse generators are well known in the art.

As shown in FIG. 5, the fixation device 56 of the tissue anchor 50 is secured to the endocardium 38 to anchor the device 82 within the heart 12 such that the substrate 84 is spaced apart from endocardium 38. Voltage pulses can be generated at the substrate 84 to produce an electrical potential between the substrate 84 and the endocardium 38. As the device 82 is maintained in the heart 12, at least one trabecular fiber 58 forms between the endocardium 38 and the substrate 84. In the embodiment shown in FIG. 5, a plurality of trabecular fibers 58 are formed. In the embodiment shown in FIG. 5, the trabecular fibers 58 extending between the substrate 84 and ventricular wall 46 and the anchor 50 extending between the substrate 84 and another part of the ventricular wall 46 serve to connect the different portions of the ventricular wall 46 to each other with the new contractile/conductile heart muscle tissue of the trabecular fibers 58. So disposed, the substrate 84 and the trabecular fibers 58 with their contractile heart muscle tissue can serve to strengthen the ventricular wall to repair damage due to thinning of the ventricular wall 46 or to an infarction in the ventricular wall 46. Not wishing to be bound by any theory, it is believed that the voltage pulses at the substrate 84 may further stimulate the growth of the trabecular fibers 58.

Figure 6:
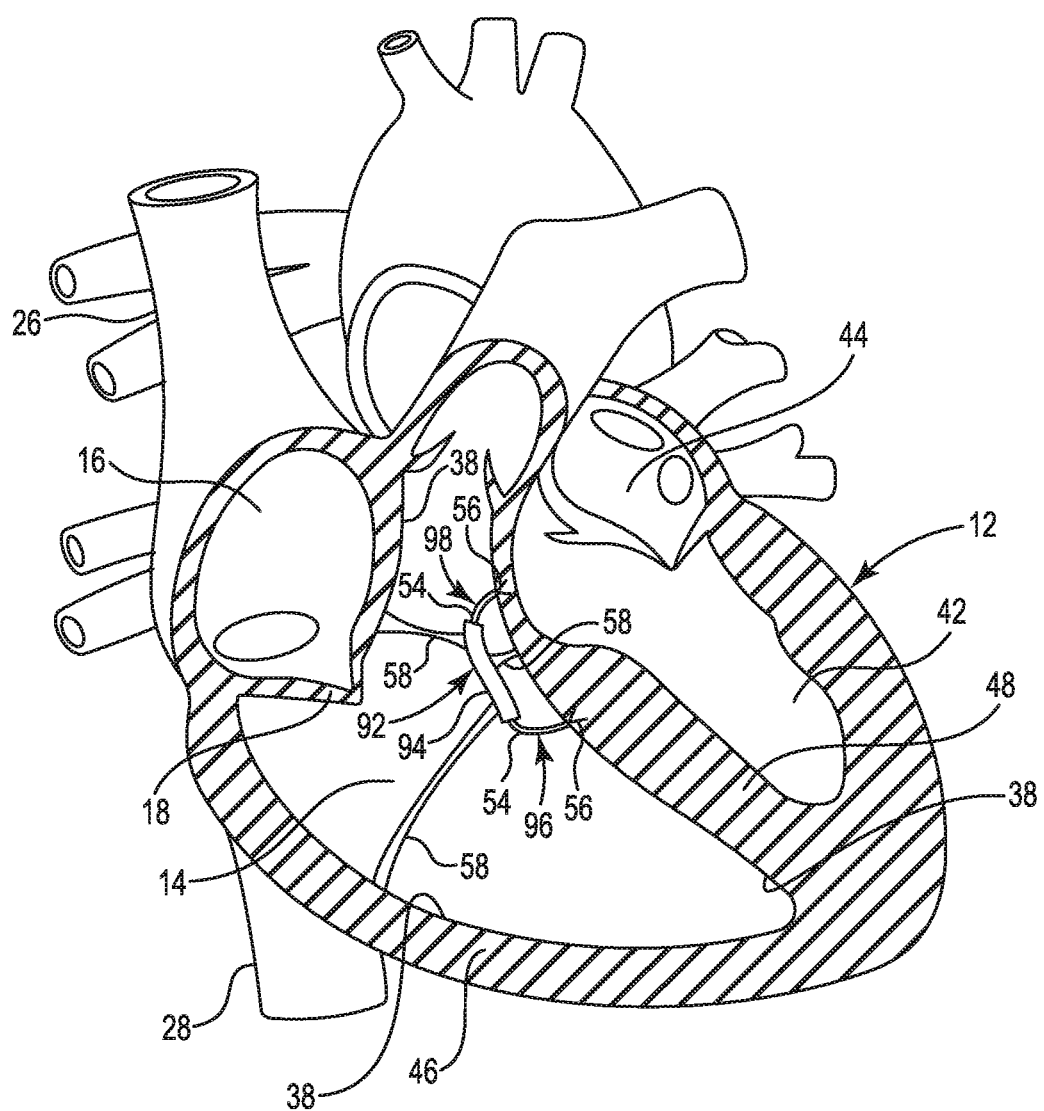
FIG. 6 is an enlarged schematic view of the heart 12 of FIG. 1 illustrating another device for stimulating the growth of at least one trabecular fiber, in accordance with embodiments of the present disclosure.

FIG. 6 is an enlarged schematic view of the heart 12 of FIG. 1 illustrating another embodiment. FIG. 6 illustrates a device 92, according to some embodiments, implanted into the endocardium 38 of the septum 48. As shown in FIG. 6, the device 92 includes a substrate 94, a first tissue anchor 96, and a second tissue anchor 98. The first tissue anchor 96 and the second tissue anchor 98 can each be substantially similar to the tissue anchor 50 described above, including a linking section 54 and a fixation device 56. In the embodiment shown in FIG. 6, the first tissue anchor 96 and the second tissue anchor 98 are connect to opposite ends of the substrate 94. As shown in FIG. 6, the substrate 94 can be substantially similar to substrate 52 described above in reference to FIG. 2. In other embodiments, the substrate 94 can be substantially similar to substrate 74, and the device 92 can further include a power supply 76 and pulse generator 78 as described above in reference to FIG. 4. In still other embodiments, the substrate 94 can be substantially similar to substrate 84 described above in reference to FIG. 5.

As shown in FIG. 6, the first tissue anchor 96 and the second tissue anchor 98 are secured the endocardium 38 of the septum 48 to anchor the device 92 within the heart 12 such that the substrate 92 is spaced apart from the endocardium 38. As the device 92 is maintained in the heart 12, at least one trabecular fiber 58 forms between the endocardium 38 and the substrate 94. In the embodiment shown in FIG. 6, the trabecular fibers 58 are formed between the substrate 94 and the endocardium 38 on the tricuspid valve 18, the ventricular wall 46, and the septum 48.

In the embodiment shown in FIG. 6, the trabecular fibers 58 extending between the substrate 94 and septum 48 and between the substrate 94 and the tricuspid valve 18 serve to connect a portion of the tricuspid valve 18 to the septum 48 with the new contractile heart muscle tissue of the trabecular fibers 58. So disposed, the substrate 94 and the trabecular fibers 58 with their contractile heart muscle tissue can alter the shape of the heart 12 to repair damage due a misalignment in the tricuspid valve 18 resulting in regurgitation by reshaping the heart 12. However, the trabecular fiber 58 extending between the substrate 94 and the ventricular wall 46 may not be necessary and may, in some instances, interfere with the repair effected by the substrate 94 and the other trabecular fibers 58.

Figure 7A:
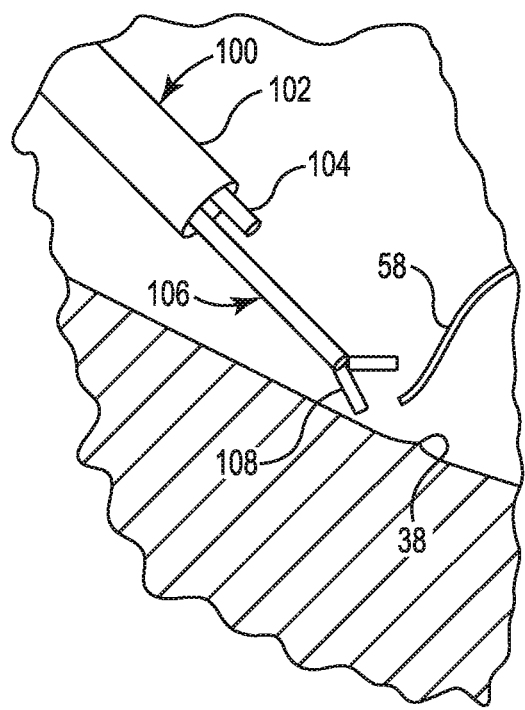
FIGS. 7A and 7B are enlarged schematic views of a portion of the heart of FIG. 6 illustrating the removal of an unnecessary trabecular fiber, in accordance with embodiments of the present disclosure.
Figure 7B:
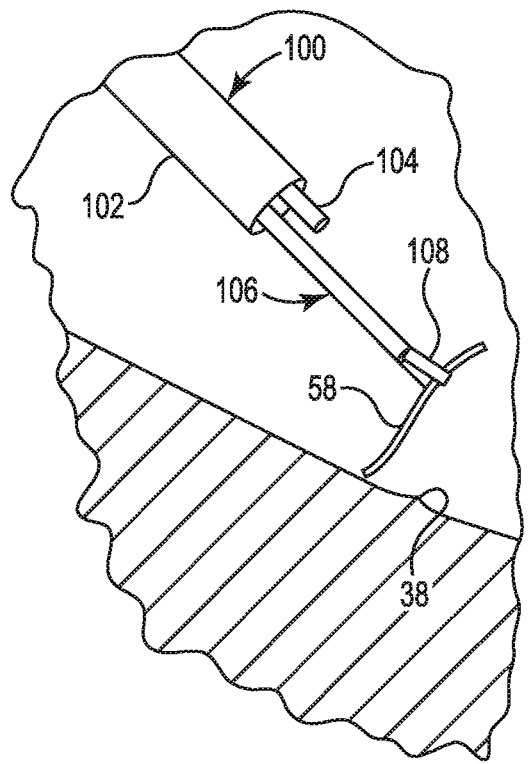

FIGS. 7A and 7B are enlarged schematic views of a portion of the heart 12 of FIG. 6 illustrating the removal of the unnecessary trabecular fiber 58 in accordance with embodiments. FIGS. 7A and 7B show a tool 100 for imaging and extracting the trabecular fibers 58. The tool 100 can include a catheter 102, a visualization device 104, and a forceps device 106. The forceps device 106 can include a pair of jaws 108. The pair of jaws 108 can be used to cut and/or grasp tissue, such as the trabecular fiber 58. The catheter 102 can include a plurality of lumens (not shown) extending the length of the catheter 102 for accommodating the visualization device 104 and the forceps device 106. The catheter 102 can be maneuvered into the right ventricle 14 as described above for catheter 30 in reference to FIG. 1.

In some embodiments, the catheter 102 can be, for example, a SpyGlass® Catheter from Boston Scientific Corporation, Natick, Mass. In some embodiments, the visualization device 104 can be a fiber-optic based device, for example, a SpyGlass® Direct Visualization Probe from Boston Scientific Corporation, Natick, Mass. In other embodiments, the visualization device 104 can include a solid-state camera, a transparent balloon (not shown) extending around the camera, and a source of saline (not shown) for inflating the transparent balloon to enhance direct visualization by displacing blood proximate to the trabecular fiber 58. In some embodiments, the forceps device 106 can be, for example, a SpyBite® Biopsy Forceps from Boston Scientific Corporation, Natick, Mass. In some embodiments, the tool 100 can further include a separate light source (not shown).

Figure 8:
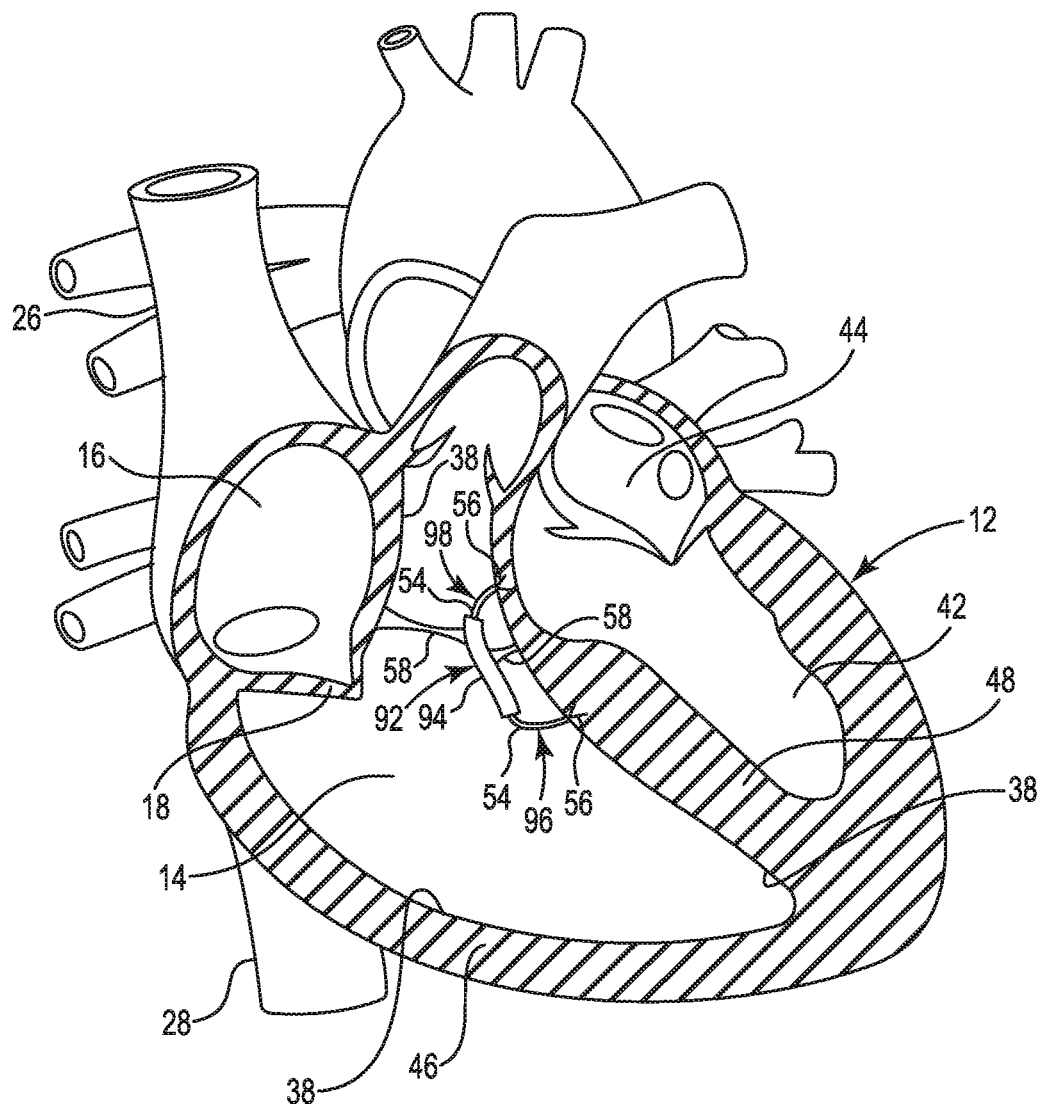
FIG. 8 is a schematic view of the heart of FIG. 6 after removal of the unnecessary trabecular fiber as shown in FIGS. 7A and 7B.

As shown in FIG. 7A, removing the trabecular fiber 58 can include cutting away the trabecular fiber 58 from the endocardium 38 by operation of the pair of jaws 108 of the forceps device 106. In a similar fashion, the trabecular fiber 58 can be cut from the substrate 94 by operation of the pair of jaws 108 of the forceps device 106 (FIG. 6). As shown in FIG. 7B, once the trabecular fiber 58 is cut away from both the endocardium 38 and the substrate 94, the pair of jaws 108 can grasp the trabecular fiber 58. The forceps device 106 can be withdrawn through the lumen in the catheter 102 to remove the entire trabecular fiber 58 from the heart 12. The process may be repeated for removing any additional unnecessary trabecular fibers 58. Although the process is described as cutting away the trabecular fiber 58 from the endocardium 38, and then cutting away the trabecular fiber 58 from the substrate 94, it is understood that embodiments may include cutting away the trabecular fiber 58 from the substrate 94, and then cutting away the trabecular fiber 58 from the endocardium 38. FIG. 8 is a schematic view of the heart 12 of FIG. 6 after removal of the unnecessary trabecular fiber 58.

Figure 9:
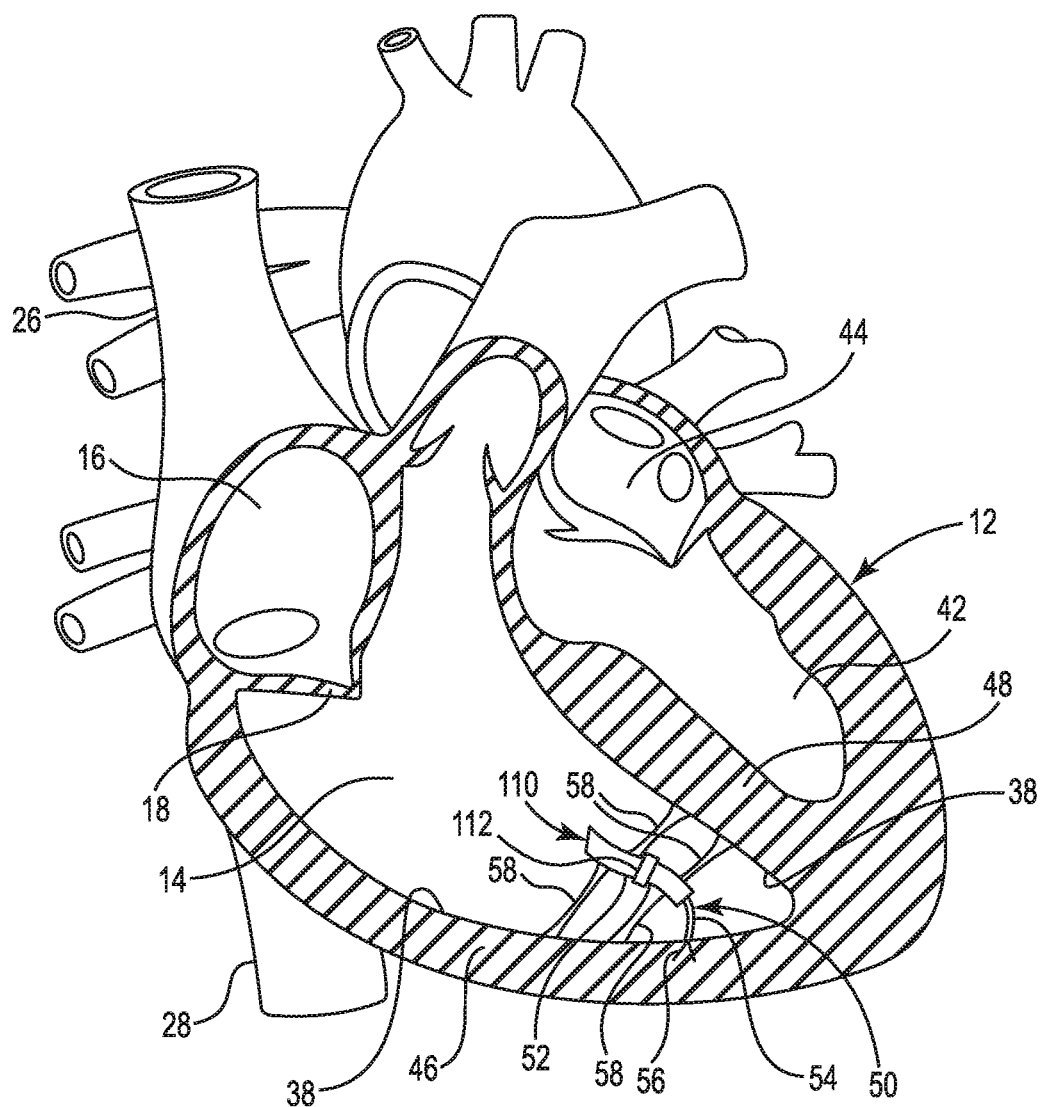
FIG. 9 is an enlarged schematic view of the heart 12 of FIG. 1 illustrating another device for stimulating the growth of at least one trabecular fiber, in accordance with embodiments of the present disclosure While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

FIG. 9 is an enlarged schematic view of the heart 12 of FIG. 1 illustrating yet another embodiment. FIG. 9 illustrates a device 110, according to some embodiments, implanted into the endocardium 38 of the ventricular wall 46. As shown in FIG. 9, the device 110 includes a tissue anchor 50, a substrate 52, and at least one drug eluting collar 112. The tissue anchor 50 and the substrate 52 are as described above in reference to FIG. 2. In the embodiment shown in FIG. 9, the collar 112 is disposed around the middle of the substrate 52. However, in other embodiments, the collar 112 can be disposed anywhere along the substrate 52.

The drug eluting collar 112 can include an anti-inflammatory or immunosuppressive biologic or pharmaceutical agent, such as a steroid. The steroid can be, for example, a glucocorticoid such as dexamethasone acetate or hydrocortisone. The steroid can be disposed within a liquid silicone rubber (LSR) matrix such that the steroid can elute from the LSR matrix. The collar 112 may be formed by mixing the steroid into the LSR before the LSR cures. In some embodiments, the steroid may elute from the LSR matrix over an extended period of time. In some embodiments, the collar 112 may include a steroid dose of as little as 0.20 milligrams (mg), 0.30 mg, 0.40 mg, or 0.50 mg, or as great as 0.70 mg, 0.80 mg, 0.90 mg or 1.0 mg, or any amount between any of the preceding values. In some embodiments, the collar 112 may include a steroid dose ranging from 0.20 mg to 1.0 mg, from 0.30 mg to 0.90 mg, from 0.40 mg to 0.80 mg, or from 0.50 mg to 0.70 mg. In some embodiments, the collar 112 may include as steroid dose of about 0.60 mg.

As with device 40 described above, the tissue anchor 50 can include a linking section 54 and a fixation device 56. The linking section 54 connects the fixation device 56 to the substrate 52, connecting the tissue anchor 50 to the substrate 52.

As shown in FIG. 9, the fixation device 56 of the tissue anchor 50 is secured into the endocardium 38 to anchor the device 110 within the heart 12 such that the substrate 522 is spaced apart from endocardium 38. An anti-inflammatory or immunosuppressive biologic or pharmaceutical agent, such as the steroid dexamethasone acetate, can elute from the collar 112. As the device 110 is maintained in the heart 12, at least one trabecular fiber 58 forms between the endocardium 38 and the substrate 52. In the embodiment shown in FIG. 9, a plurality of trabecular fibers 58 are formed. In the embodiment shown in FIG. 9, the trabecular fibers 58 extending between the substrate 52 and ventricular wall 46, and the trabecular fibers 58 extending between the substrate 52 the septum 48 serve to connect the ventricular wall 46 to the septum with the new contractile/conductile heart muscle tissue. So disposed, the substrate 52 and the trabecular fibers 58 with their contractile/conductile heart muscle tissue can serve to repair damage due to thinning of the ventricular wall 46 or to an infarction in the ventricular wall 46, thus improving cardiac output. Not wishing to be bound by any theory, it is believed that the anti-inflammatory or immunosuppressive biologic or pharmaceutical agent eluting from the collar 112 may further stimulate the growth of the trabecular fibers 58.

In all embodiments described above, the device for producing at least one trabecular fiber within a heart to repair the heart is configured to be contained entirely within the ventricle. That is, the device is sized and shaped to be contained entirely within the ventricle to enhance the minimally invasive nature of the device.

In all embodiments described above, for the sake of brevity, the device for producing at least one trabecular fiber within a heart to repair the heart is implanted in the right ventricle. However, it is understood that in other embodiments of the disclosure, the device may be implanted additionally or alternatively in the left ventricle.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A device for producing a trabecular fiber within a ventricle of a heart, the device comprising:
 a substrate formed of a non-rigid material;
 a first tissue anchor connected to the substrate; and
 a second tissue anchor connected to an opposite end of the substrate from the first tissue anchor, the first tissue anchor and the second tissue anchor each including a fixation device and a linking section coupling the fixation device to the substrate, wherein the device is configured to be contained entirely within the ventricle.

2. The device of claim 1, wherein the substrate includes at least one electrode.

3. The device of claim 2, wherein the device is configured to be connected to a pulse generator and a power supply external to the heart by an electrical lead, the electrical lead connecting the pulse generator and the power supply to the at least one electrode to generate a plurality of voltage pulses at the at least one electrode.

4. The device of claim 2, wherein the device further includes a pulse generator and a power supply, the pulse generator and the power supply electrically connected to the at least one electrode to generate a plurality of voltage pulses at the least one electrode.

5. The device of claim 1, wherein the substrate includes a ribbon of electro-spun fibers.

6. The device of claim 1, wherein the substrate is formed of at least one of a polyurethane polymer, a polyester polymer, a silicone polymer, a styrene-isobutylene-styrene block copolymer, an expanded polytetrafluoroethylene polymer, collagen, hyaluronan, cellulose, fibrin, fibrinogen, and fibronectin.

7. The device of claim 1, further including at least one drug eluting collar disposed around the substrate, the collar including a steroid.

* * * * *